(12) United States Patent
Guo

(10) Patent No.: US 6,895,977 B2
(45) Date of Patent: May 24, 2005

(54) DENTAL FLOSSING TOOL

(76) Inventor: Chongwei Guo, Hospital Development Zone, No. 22 First Sreet, Economic & Technical Development Zone, Tianjin City (CN), 300457

(*) Notice: Subject to any disclaimer, the term of this patent is extended or adjusted under 35 U.S.C. 154(b) by 0 days.

(21) Appl. No.: 10/449,047

(22) Filed: May 30, 2003

(65) Prior Publication Data

US 2003/0230320 A1 Dec. 18, 2003

Related U.S. Application Data

(63) Continuation of application No. PCT/CN01/01602, filed on Feb. 5, 2001.

(30) Foreign Application Priority Data

Dec. 8, 2000 (CN) .................. 00260259 U

(51) Int. Cl.[7] .............................................. A61C 15/00
(52) U.S. Cl. ..................................................... 132/325
(58) Field of Search ................................. 132/323, 324, 132/325, 326, 327, 328

(56) References Cited

U.S. PATENT DOCUMENTS

| 3,747,611 A | 7/1973 | Bennington | |
| 4,342,324 A | 8/1982 | Sanderson | |
| 4,657,034 A | 4/1987 | Koski | |
| 5,183,065 A | * 2/1993 | Mason | 132/323 |
| 5,224,502 A | 7/1993 | Walker, Jr. | |
| 5,251,651 A | 10/1993 | Mason | |
| 5,348,032 A | * 9/1994 | Mason | 132/325 |
| 5,657,780 A | * 8/1997 | Giacopuzzi | 132/325 |

FOREIGN PATENT DOCUMENTS

SN 2218538 Y 1/1996

* cited by examiner

Primary Examiner—Cary E. O'Connor
(74) Attorney, Agent, or Firm—Rod D. Baker; Peacock Myers & Adams, PC

(57) ABSTRACT

A dental flossing tool for dispensing floss for cleaning the user's teeth. A handle body surrounds a cavity and has a lead riser from which dental floss is dispensed for use. The floss is wound upon a spool that rotates inside the cavity. Floss is paid out from the spool and emerges from a hole in the tip of the lead riser. A button or handle is slidably mounted upon the apparatus for controlling the longitudinal movement of a retainer within the cavity of the apparatus. By sliding the button handle forward and backward, the user can disengage and engage the retainer with a baffle attached to the spool inside the body of the apparatus. When the retainer is in contact with the baffle, the spool is prevented from rotating, thereby stopping any further floss from being dispensed. When the retainer is disengaged out of contact with the baffle, the spool is free to rotate to pay out floss. A removable protector is provided for covering the lead riser and a floss cutter blade attached to the exterior of the apparatus. The protector can be removed to the back end of the apparatus to extend its graspable portion for easier handling.

8 Claims, 1 Drawing Sheet

DENTAL FLOSSING TOOL

CROSS-REFERENCE TO RELATED APPLICATIONS

Figure 1:
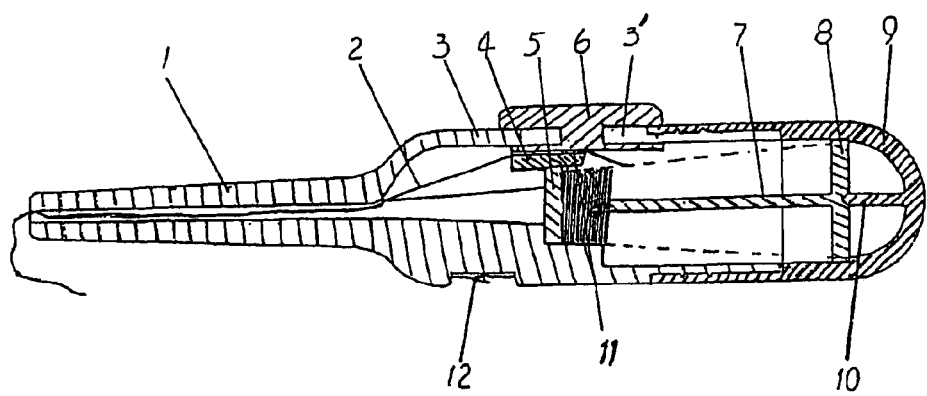

This application is a continuation of Patent Cooperation Treaty Application Serial No. PCT/CN01/01602 having an international filing date of Dec. 5, 2001, which claimed priority to Chinese patent application Serial No. 00260259.8, filed Dec. 8, 2000, entitled "A Kind of Dental Flossing Tool," to which priority is claimed and the teachings of which are incorporated herein by reference.

THE TECHNICAL FIELD

The present invention relates to the tooth cleaning tool, and particularly relates to the dental flossing tool using the dental floss to clean the teeth.

THE TECHNICAL BACKGROUND

The decayed tooth is the most common dental disease being dangerous to the human health, the decayed tooth and its secondary infection bring great harm to people's mouth and even the whole body, the people in different countries of different age, race,region,occupation and male or female have all been affected by the decayed tooth which is in high incidence, the world health organization has ranked it as one of the three diseases being harmful to human health.

Concerning the above, cleaning teeth has become the indispensable thing in our usual life, and the dental floss has been gradually accepted as the accessorial product of the dental cleaning, since the dental floss is the effective tool for removing the bacterium fleck, the soft dirt and the remaining food between the adjacent teeth surfaces and the clearance between the teeth by mechanical manner, and it is difficult to clean the teeth thoroughly by just using the toothbrush, it is proved by the expert that the decayed tooth could be decreased 30% by accurate using the dental floss; and the dental flossing tool in the shape of catapult is the usual traditional appliance for convenient using the dental floss, which needs to mount the dental floss to the both ends of the said appliance at any moment. The once use dental flossing tool has been assembled the dental floss during manufacturing, although it does not need to mount the dental floss at any moment, but it is not easy to control while cleaning the teeth, which results not ideal cleaning effect.

The present applicant has disclosed a dental flossing tool being convenient to control and carry in the patent ZL94214468.6, which is consisted of lead riser with the handle and the tooth wire wheel within the handle, the dental floss is induced from the lead riser, and the handle is disposed with the locking wire pusher for locking the dental floss. It is shown by the practice that since the axis of the dental floss wheel is intersected with the handle axis vertically, which leads to the limitation of the length of the dental floss wound around the dental floss wheel, and thus the use times is limited and also the dental flossing tool could be carried only by equipping the storage box.

THE INVENTIVE CONTENT

The main object of the present invention is to provide a kind of dental flossing tool which could close in the dental floss while being carried and stored in order to prevent it from being polluted, it could also prevent the finger from direct contacting to the dental floss in the gap between the adjacent teeth.

Another object of the present invention is to provide an improved dental flossing tool, which is in reasonable structure, equipping longer dental floss, convenient to use and easy to take.

The above objects are realized by the following technical scheme: the handle of the present invention is composed of a cavity handle body having a lead riser and a handle cover connecting to the port of the handle body. The said handle body has longitudinal sliding groove. The two sides of pushing handle of locking wire are slidely engaged to the sliding groove. A spool of dental floss are provided lengthways in the handle, whose circular front baffle supporting axis of handle cover. The arranges a retainer having thread hole on the bottom surface of the pushing handle of locking wire, the said retainer frictionally engaging to the circular front baffle of the spool at the position of locking wire. The front end of the handle body arranges the protector of said lead riser.

The said handle body and handle cover are attached by the separately arranged circular groove and protrusion.

The thread cutter is disposed at the outer side of the handle body, the said thread cutter is a thin slice which is turnup and has a sharp edge.

The said retainer on the bottom surface of the pushing handle of locking wire is disposed with the wedge-shaped slant being matched with the peripheral slant of the circular front baffle of the spool of the dental floss.

The said protector could sheathe to the handle cover.

The present invention provides a hand-held dental flossing tool, one end of the dental floss is gone deep into the mouth through the lead riser in order to prevent the finger from contacting to the mouth, the other hand holds the other end of the dental floss, therefor the dental floss is easy to control by cooperation of the two hands, and also the inner attached dental floss could be used for a long time without taking the storage box.

The further explanation of the present invention is made by referencing the drawings as follows.

THE BRIEF DESCRIPTION OF THE DRAWINGS

Figure 2:
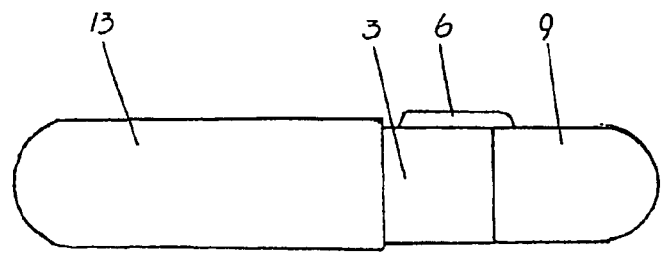
Figure 3:
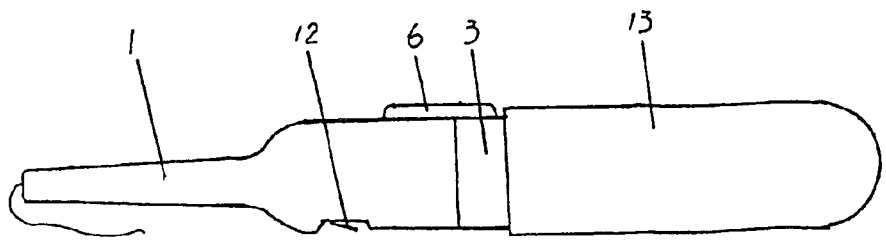

The FIG. 1 is the sectional schematic view of the main structure of the dental floss of the present invention;

The FIG. 2 is the appearance view of the dental flossing tool equipped with the protector of the present invention;

The FIG. 3 is the appearance view of the dental flossing tool in use of the present invention.

THE DETAILED DESCRIPTION OF THE EMBODIMENTS

As shown in FIG. 1, the front end of the handle body 3 defines the lead riser 1. The handle cover 9 is sheathed over the back end of the handle body and preferably is attached thereto by the engagement of a circular protrusion on the handle body 3 into a circular groove in the interior of the handle cover 9. The handle body 3 and cover 9 enclose a hollow cavity, in which the spool 7 of dental floss is longitudinally disposed. A circular front baffle 5 is supported by the first of three protruding annular stages or steps, of increasing diameter, defined on the interior wall of the handle body 3, as seen in cross section in FIG. 1. The rear baffle 8 also has a circular shape, and is supported by the engagement of the gimlet point of the inner shaft 10 into a central fosse in the baffle 8. The inner shaft 10 extends axially forward from the inside of the handle cover 9. The spool 7 having dental floss wound thereon thus is rotatably positioned within the cavity, being supported by the point contact between the rear baffle 8 and the inner shaft 10, and by the sliding contact between the front baffle 5 and the first stage or step on the inside of the handle body 3. The handle body 3 has a longitudinal slot or sliding groove 3' defined therein. The pushing handle 6 has a generally "I" shaped cross section, as seen in FIG. 1, with portions of the pushing handle 6 disposed on both sides (interior and exterior) of the wall of the handle body 3, thereby to attach the pushing handle 6 to the handle body in a manner permitting the pushing handle to move slidably along said groove, but without becoming detached from the apparatus. A retainer 4 is disposed upon the bottom or inner side of the pushing handle 6. The retainer 4 is somewhat wedge-shaped, the inner face of the retainer 4 defining an incline or slant. The peripheral edge of the circular front baffle 5 defines a slant complementary to the angle or degree of slant of the retainer 4. At or near the interface of the retainer 4 and the pushing handle 6, there is defined through the retainer 4 a longitudinal hole or channel 11 to permit the passage of a strand of dental floss 2 from the spool 7 past the retainer 4. The dental floss 2 thus is paid out from the spool 7, past the retainer 4, and is induced from a thread hole in the distal tip of the lead riser 1, as shown in FIG. 1. A floss cutter 12, having a turned-up thin slice of metal with a sharp edge, is provided on the exterior of the handle body 3.

A protector 13 according to the invention is removably disposable over the lead riser 1 at the front end of the handle body 3, as shown in FIG. 2, to cover the lead riser and close the floss cutter 12 (FIG. 1) when the apparatus is not in use.

The protector 13 may be removably sheathed over the hand cover 9 while the apparatus is in use, as seen in FIG. 3. When the protector 13 is securely but removably attached over the handle body 3, the overall length of the apparatus is reduced, yet the graspable portion of the apparatus is effectively prolonged or extended for more convenient holding of the apparatus in use.

The dental flossing tool of the present invention may be manufactured from low-cost innocuous polyethylene. The length of the dental floss wound upon the spool 7 typically is 25 meters, which permits the apparatus of the invention to be repeatedly used many times without the need to exchange the spool of dental floss. In the use of the apparatus, the pushing handle 6 is pushed forward (sliding along the sliding groove 3') by the user, and the protector 13 is removed from the front of the apparatus to expose the lead riser 1 and sheathed over the handle cover 9 in order to extend the graspable length of the handle body. When sufficient length of dental floss 2 has been pulled out of the interior of the handle body 3, the user slides the pushing handle 6 rearward in the groove 3' in order to frictionally contact the slanted face of the retainer 4 against the slanted periphery of the circular front baffle 5, to stop rotation of the front baffle 5 and thus firmly lock the dental floss 2 from further unwinding. Used dental floss 2 can be cut away using the floss cutter 12.

The dental floss 2 is wound around the spool 7 for storage within the interior cavity of the handle body 3. In the use of the invention, floss 2 can be unwound from the spool, paid out through the lead riser 1, and locked against further unwinding. The lead riser 1 can be inserted deep into the user's mouth, and the teeth conveniently cleaned by the cooperation of the apparatus with the user's other hand grasping the free end of the floss. The invention improves the healthfulness of flossing by reducing the contact between the user's hands and the floss. When the dental floss 2 is exhausted, the back handle cover 9 may be opened or removed, and a replacement spool of new floss disposed in the handle body for further use of the apparatus.

In regard to the above, the dental flossing tool of the present invention is in simple structure and easy to carry. Which is a novel design and the equivalent changes are all within the protected scope limited by the appended claims.

What is claimed is:

1. An apparatus for dispensing dental floss comprising:
  a handle body having an exterior and defining:
    an interior cavity;
    a longitudinal groove; and
    a lead riser;
  a spool of dental floss within said cavity, said spool rotatable around a longitudinal axis, and comprising a substantially circular front baffle; and
  a pushing handle disposed in said groove and slidable longitudinally along said groove, said pushing handle having a retainer portion disposed within said interior cavity, said retainer portion defining therein a longitudinal hole for the passage of floss there-through;
  wherein a free end of said floss is dispensable from said rotatable spool, through said hole, and out of said lead riser to the exterior of said body, and wherein further said pushing handle is controllably slidable, longitudinally substantially parallel to said axis, between a locked position wherein said retainer frictionally engages said front baffle to prevent rotation of said spool, and an unlocked position wherein said retainer is disengaged from said front baffle thereby permitting said spool to rotate to permit dispensing of floss.

2. The apparatus of claim 1 wherein said handle body comprises a handle cover opposite said lead riser.

3. The apparatus of claim 2 wherein said handle cover is removably secured by means of at least one circular protrusion on said exterior engaged with a corresponding circular groove in said handle cover.

4. The apparatus of claim 2 further comprising:
  a floss cutting blade disposed on said exterior of said handle body; and
  a protector, engageable with said handle body, for covering said lead riser and said cutting blade when said apparatus is not in use.

5. The apparatus of claim 4 wherein said protector is engageable over said handle cover when said apparatus is in use.

6. The apparatus of claim 1 wherein said retainer comprises a wedge shaped portion, and said front baffle defines a slanted periphery, and further wherein the angle defining said wedge-shaped portion is complementary to the angle defining said slanted periphery, and wherein further said wedge-shaped portion and said slanted periphery are in flush contact when said pushing handle is in the locked position.

7. An apparatus for dispensing dental floss comprising:
  a handle body having an exterior and defining:
    an interior cavity;
    a longitudinal groove; and
    a lead riser;
  a spool of dental floss within said cavity, said spool rotatable around a longitudinal axis, and comprising a substantially circular front baffle;
  a pushing handle disposed in said groove and slidable longitudinally along said groove, said pushing handle having a retainer portion disposed within said interior cavity, said retainer portion defining therein a longitudinal hole for the passage of floss there-through;
  a floss cutting blade disposed on said exterior of said handle body; and
  a protector, removably engageable with said handle body to cover said lead riser and said cutting blade when said apparatus is not in use, and removably engageable over said handle cover when said apparatus is in use;

wherein a free end of said floss is dispensable from said rotatable spool, through said hole, and out of said lead riser to the exterior of said body, and wherein further said pushing handle is controllably slidable, longitudinally substantially parallel to said axis, between a locked position wherein said retainer frictionally engages said front baffle to prevent rotation of said spool, and an unlocked position wherein said retainer is disengaged from said front baffle thereby permitting said spool to rotate to permit dispensing of floss.

8. An apparatus for dispensing dental floss comprising:
 a handle body having an exterior and defining:
  an interior cavity;
  a longitudinal groove; and
  a lead riser;
 a spool of dental floss within said cavity, said spool rotatable around a longitudinal axis, and comprising a substantially circular front baffle; and
 a pushing handle disposed in said groove and slidable longitudinally along said groove, said pushing handle having a retainer portion disposed within said interior cavity, said retainer portion defining therein a longitudinal hole for the passage of floss there-through;

wherein said retainer comprises a wedge shaped portion, and said front baffle defines a slanted periphery, and further wherein the angle defining said wedge-shaped portion is complementary to the angle defining said slanted periphery, and wherein further said wedge-shaped portion and said slanted periphery are in flush contact when said pushing handle is in the locked position; and wherein further a free end of said floss is dispensable from said rotatable spool, through said hole, and out of said lead riser to the exterior of said body, and wherein further said pushing handle is controllably slidable, longitudinally substantially parallel to said axis, between a locked position wherein said retainer frictionally engages said front baffle to prevent rotation of said spool, and an unlocked position wherein said retainer is disengaged from said front baffle thereby permitting said spool to rotate to permit dispensing of floss.

* * * * *